US010660790B2

(12) United States Patent
Barnett et al.

(10) Patent No.: US 10,660,790 B2
(45) Date of Patent: May 26, 2020

(54) HEATING PAD (71) Applicant: TRIODYNE SAFETY SYSTEMS, L.L.C., Glenview, IL (US)

(72) Inventors: Ralph Lipsey Barnett, Wilmette, IL (US); James R. Wingfield, Crystal Lake, IL (US)

(73) Assignee: TRIODYNE SAFETY SYSTEMS, L.L.C., Glenview, IL (US)

( * ) Notice: Subject to any disclaimer, the term of this patent is extended or adjusted under 35 U.S.C. 154(b) by 39 days.

(21) Appl. No.: 15/820,649

(22) Filed: Nov. 22, 2017

(65) Prior Publication Data

US 2018/0168854 A1 Jun. 21, 2018

Related U.S. Application Data

(63) Continuation-in-part of application No. 15/338,570, filed on Oct. 31, 2016, now abandoned, which is a continuation-in-part of application No. 14/014,132, filed on Aug. 29, 2013, now Pat. No. 9,504,602.

(60) Provisional application No. 61/694,642, filed on Aug. 29, 2012.

(51) Int. Cl.
| A61B 7/00 | (2006.01) |
| A61F 7/00 | (2006.01) |
| A61F 7/08 | (2006.01) |
| H05B 1/02 | (2006.01) |
| H05B 3/34 | (2006.01) |
| A61F 7/02 | (2006.01) |

(52) U.S. Cl.
CPC ............... *A61F 7/007* (2013.01); *A61F 7/08* (2013.01); *H05B 1/025* (2013.01); *H05B 3/34* (2013.01); *A61F 2007/0086* (2013.01); *A61F 2007/0093* (2013.01); *A61F 2007/0095* (2013.01); *A61F 2007/0296* (2013.01); *H05B 2203/035* (2013.01)

(58) Field of Classification Search
CPC .. A61F 7/007; A61F 7/08; H05B 3/34; H05B 1/025
See application file for complete search history.

(56) References Cited

U.S. PATENT DOCUMENTS

| 2,543,620 | A | * | 2/1951 | Anderson | ............... H05B 3/342 219/212 |
| 4,638,436 | A | | 1/1987 | Badger et al. | |
| 5,432,322 | A | | 7/1995 | Ingram et al. | |
| 2006/0195168 | A1 | | 8/2006 | Dunbar et al. | |
| 2007/0016271 | A1 | | 1/2007 | Hammond | |
| 2008/0053979 | A1 | | 3/2008 | Toya et al. | |
| 2012/0279953 | A1 | | 11/2012 | Augustine et al. | |
| 2014/0074196 | A1 | | 3/2014 | Barnett et al. | |
| 2017/0048926 | A1 | | 2/2017 | Barnett et al. | |

* cited by examiner

*Primary Examiner* — Linda C Dvorak
*Assistant Examiner* — Ryan T Clark
(74) *Attorney, Agent, or Firm* — Pauley Erickson & Kottis (57) ABSTRACT

An improved heating pad which minimizes or eliminates skin burns due to improper uses in one or more of several ways: by monitoring a total electric power input or output of the heating pad; by monitoring an absolute temperature of each surface of the heating pad; by monitoring a temperature difference between each surface of the heating pad, where a small temperature difference indicates that both sides of the heating pad are covered; and/or by monitoring the duty cycle of a heating element, where a large off portion of the duty cycle indicates both sides of the heating pad are covered.

20 Claims, 5 Drawing Sheets

HEATING PAD

CROSS REFERENCE TO RELATED APPLICATION

This application a continuation-in-part of U.S. patent application Ser. No. 15/338,570, filed 31 Oct. 2016, which is a continuation-in-part of U.S. patent application Ser. No. 14/014,132, filed 29 Aug. 2013, which claims priority to U.S. Provisional Patent Application 61/694,642, filed 29 Aug. 2012. The parent applications are hereby incorporated by reference herein and made a part hereof, including but not limited to those portions which specifically appear hereinafter.

BACKGROUND OF THE INVENTION

Field of the Invention

This invention is directed to an improved electric heating pad which prevents burns resulting from improper use. More specifically, this invention is directed to an improved electric heating pad which monitors total energy input or output, monitors temperatures of surfaces of the heating pad, and/or monitors a duty cycle of an internal thermostat, to detect when the heating pad is covered.

Discussion of Related Art

Electric heating pads are used by many for pain relief and to improve local blood circulation. However, use of electric heating pads is also associated with severe dangers including shock/electrocution, fire, and skin burns.

Underwriters Laboratories Inc. (UL) has developed and promulgated design rules that effectively mitigated the dangers of shock/electrocution and fire. However, UL has not undertaken a technical program that addresses the skin burn problem. Nevertheless, many heating pad manufacturers have falsely represented that their compliance with UL standards has ameliorated the skin burn propensity of their pads.

For the most part, heating pad manufacturers have attempted to minimize the danger of skin burn injuries with the use of on-product and in-manual warnings that have been promulgated by UL, the Food and Drug Administration (FDA), and Consumer Product Safety Commission (CPSC). For example Table 1 shows a typical on-product warning label for an electric heating pad.

TABLE 1

| DANGER |
| --- |
| TO REDUCE THE RISK OF BURNS, ELECTRIC SHOCK, AND FIRE, THIS PRODUCT MUST BE USED IN ACCORDANCE WITH THE FOLLOWING INSTRUCTIONS: BURNS CAN OCCUR REGARDLESS OF CONTROL SETTING, CHECK SKIN UNDER PAD FREQUENTLY. DO NOT SIT ON, LEAN AGAINST, OR CRUSH PAD-AVOID SHARP FOLDS, ALWAYS PLACE PAD ON TOP OF AND NOT UNDER YOUR BODY. NEVER PLACE PAD BETWEEN YOURSELF AND CHAIR, SOFA, BED, OR PILLOW. DO NOT USE WHILE SLEEPING. DO NOT USE ON AN INFANT. THIS PAD IS NOT TO BE USED ON OR BY AN INVALID, SLEEPING OR UNCONSCIOUS PERSON, OR A PERSON WITH POOR BLOOD CIRCULATION OR DIABETES UNLESS CAREFULLY ATTENDED. DO |

TABLE 1-continued

| DANGER |
| --- |
| NOT USE ON AREAS OF INSENSITIVE SKIN. NEVER USE PAD WITHOUT THE CLOTH COVER IN PLACE. DO NOT USE PINS OR OTHER METALLIC MEANS TO FASTEN THIS PAD IN PLACE. DO NOT USE IN OXYGEN ATMOSPHERE. NEVER PULL THIS PAD BY THE POWER SUPPLY CORD. DO NOT USE THE POWER SUPPLY CORD AS A HANDLE. UNPLUG WHEN NOT IN USE. DO NOT USE PAD WITH LINIMENT, SALVE, OR OINTMENT PREPARATIONS THAT CONTAIN HEAT-PRODUCING INGREDIENTS, SKIN BURNS COULD RESULT. CAREFULLY EXAMINE INNER COVER BEFORE EACH USE. DISCARD THE PAD IF INNER COVER SHOWS ANY SIGN OF DETERIORATION. READ AND FOLLOW ALL INSTRUCTIONS ON BOX OR PACKED WITH PAD BEFORE USING. |

However, use of warnings has failed to reduce the burn rate. In fact, the CPSC estimates that the annual number of skin burns due to electric heating pads has increased by 33.9% from 1600 in 1995 to 2142 in 2008. Furthermore, as the number of required admonitions increases, the effectiveness of the warnings decreases as users become overwhelmed reducing the warnings to an exercise in liability proofing.

Most skin burn accidents can be attributed to three reasonably foreseeable misuses of the pads:

1. Covering both faces of the pad—increasing contact temperature or heat transfer to the body.
2. Falling asleep during use—increasing exposure time.
3. Omitting, the cloth cover—increasing both the contact temperature and the rate of heat energy transfer to the body.

Some manufacturers have eliminated the third improper use by eliminating removable covers and only including permanent covers with their heating pads. However, this approach fails to eliminate or minimize the first two improper uses.

Manufacturers have also attempted to minimize the second improper use by including a dead-man switch with their heating pads. A dead-man switch is a lever or button that must be continuously depressed to maintain operation of the pad. Should the user fall asleep during use, the user will release the dead-man switch shutting off the heating pad. However, some users have been known to circumvent the dead-man switch by tying down the dead-man switch thereby overriding the safety aspect of the dead-man switch. Other manufacturers have eliminated the dangers of users tying down dead-man switches with an on/off switch with a maximum heating time of 20 minutes. The on switch allows the user to restart the 20-minute timer any time by pushing the on button or end the session by pushing the off button. If the user falls asleep or forgets to press the off button, the built-in-timer will automatically shut the unit off for safety. However, neither the dead-man switch nor the on/off switch with an automatic timer address the first misuse identified above.

Accordingly, there is a need for an improved electric heating pad that eliminates exposure to extreme temperatures when both faces of the heating pad are covered.

SUMMARY OF THE INVENTION

A general object of the invention is to provide an improved electric heating pad which can eliminate or reduce the incident of burns due to both sides of the electric heating pad being covered during use.

Many incidents of skin burns from electric heating pads are due to consumers improperly using the heating pad by placing a cover over the heating pad and positioning the heating pad between the body and a furniture piece. Both of these improper uses confine all or most of the heat energy generated by heating elements to an area of application on the body increasing the quality and rate of heat transfer into the body. Proper use of the heating pad requires a user to place one surface of the heating pad against a body surface that is to be treated and allowing the other surface of the heating pad to be exposed to the atmosphere. The reason for this is that the total rate of heat energy transfer out of the heating pad is divided such that only about half will be transferred into the body and the rest of the heat is converted or convected away from the open side. Covering both sides of the heating pad, one by the body and the opposite by a cover or furniture, can result in nearly all of heat energy generated by the heating pad to be transferred to the skin of the user which may result in skin burns.

The heating pad device of one embodiment of this invention seeks to prevent skin burns due to covering both sides of a heating pad by monitoring and analyzing a total power input. The invention includes a method and apparatus for monitoring an electric power usage of the heating pad and determining an improper covering of the heating pad from a predetermined variation in the electric power usage. In embodiments of this invention, the improper covering causes a power usage to meet or not meet a predetermined value, such as a maximum or minimum value or a value considered as a function of time (e.g., being above or below one or more values for a predetermined time period). In other embodiments of this invention, the power usage or energy output is compared to a predetermined power curve or model. An unsafe condition is thus correlated to a predetermined power usage by the heating pad, and the heating pad can be automatically turned off by the controller, either temporarily or permanently, if the predetermined power usage occurs.

The components for method above can be integrated within the control box of the heating pad, or in a separate attachment connectable to the heating pad. In embodiments of this invention, the components are embodied as an attachment for the heating pad, connected between the heating pad plug and the power supply. The attachment can receive the plug of the heating pad, and include a plug for a wall outlet, thereby allowing use with existing heating pads. The electrical power flows through the attachment, and the power draw or usage is monitored/measured for determining an improper covering of the heating pad by comparing the monitored electric power usage or energy output to a predetermined variation in the electric power usage or energy output.

The heating pad device of another embodiment of this invention seeks to prevent skin burns due to covering both sides of a heating pad by: monitoring an absolute temperature of each surface of the heating pad; monitoring a temperature difference between each surface of the heating pad, where a small temperature difference indicates that both sides of the heating pad are covered; and by monitoring the duty cycle of the heating element, where, when at steady state operation, a large off portion of the duty cycle indicates both sides of the heating pad are covered.

The heating pad device can include a first thermocouple mounted to a first surface of the heating pad to measure a first surface temperature ($T_1$) of the heating pad and a second thermocouple mounted to a second surface of the heating pad to measure a second surface temperature ($T_2$) of the heating pad. For ease of explanation, the first surface is understood to be a surface of the heating pad which is positioned adjacent to a surface of a body and the second surface is a surface of the heating pad which faces away from the surface of a body. However, the first surface may or may not be any different from the second surface. The heating pad device of this invention further includes a processor, such as a programmable logic controller, which can monitor temperature readings of both the first surface and the second surface of the heating pad as well as monitor a heating duty cycle of a heating element of the heating pad.

In operation, the processor receives the first surface temperature ($T_1$) and the second surface temperature ($T_2$). If either temperature exceeds a maximum temperature ($T_{max}$) the processor shuts off the heating pad. In a preferred embodiment, the maximum temperature ($T_{max}$) is variable and decreases the longer the heating pad stays on to prevent burns due to prolonged exposure and relatively lower temperatures. The processor also calculates a temperature difference ($T_{diff}=T_1-T_2$) between the first surface temperature ($T_1$) and the second surface temperature ($T_2$). If the processor detects a temperature difference ($T_{diff}=T_1-T_2$) that is less than a minimum temperature difference ($T_{diff,min}$) the processor shuts off the heating pad. When the temperature difference ($T_{diff}=T_1-T_2$) is less than a minimum temperature difference ($T_{diff,min}$) it indicates that both surfaces of the heating pad are covered.

In operation, the processor also receives the heating duty cycle ($\tau$) of the heating element. The heating duty cycle ($\tau$) comprises a repeating period which includes an on portion where the heating element receives current and heating the element up and an off portion where the heating element does not receive current. The processor monitors the duty cycle to calculate a ratio that the heating pad is off $$(R_{off}), R_{off} = \frac{t_{off}}{t_{on} + t_{off}} = \frac{t_{off}}{\tau},$$

where $t_{off}$ is the portion of the duty cycle the heating element is off and $t_{on}$ is the portion of the duty cycle the heating element is on. When the processor calculates the $R_{off}$ as greater than a maximum allowable ratio ($R_{off,\,max}$), indicating that both surfaces of the heating pad are covered, the programmable logic controller shuts off the heating pad to prevent burns.

In a preferred embodiment, the heating pad of this invention further includes a permanently attached cover to prevent burns due to users using the heating pad without a cover and a switch, such as a dead-man switch and a timed switch, to prevent burns due to users falling asleep during use.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS

Figure 1:
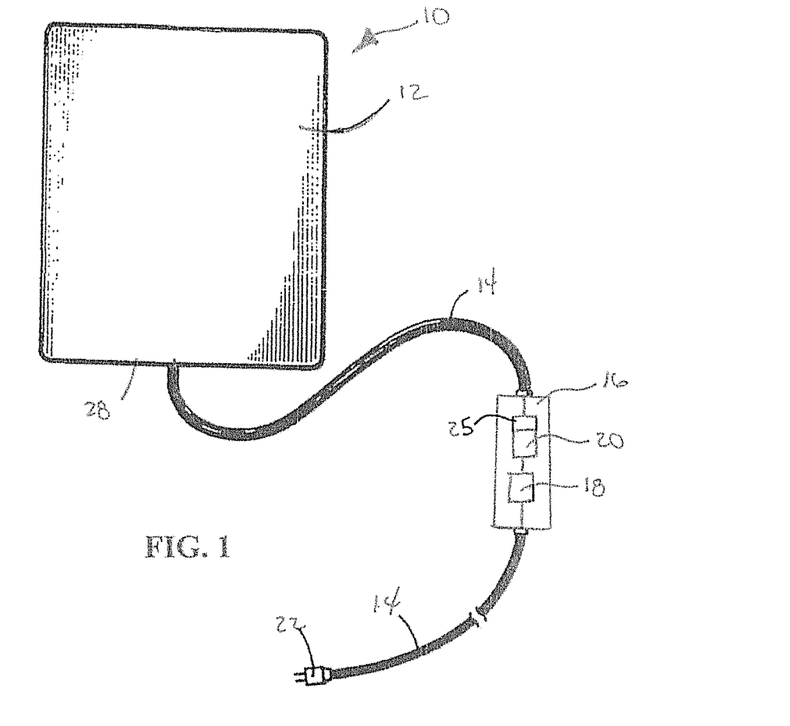
FIG. 1 is a top view of the electric heating pad according to an embodiment of this invention.

FIG. 1 shows an embodiment of an electric heating pad 10 of one embodiment of this invention which can eliminate or reduce skins burns by detecting when both sides of the electric heating pad are covered and desirably lowering the output of or shutting off the pad. The electric heating pad 10 comprises a pad 12, a cord 14, a control box 16 including an on/off switch 18 and a processor 20, and a plug 22. The processor 20 preferably comprises a programmed controller having or in combination with any suitable mechanism 25 for measuring and/or determining a power usage of the pad 10. Suitable mechanisms can be or include, for example, an ammeter, a voltmeter, or multimeter, along with a suitable calculation algorithm, and can be embodied within the control box 16.

The pad 12 preferably includes a cover 24 surrounding a heating element 26. In this embodiment, the pad 12 is generally planar with a square-shape, usefully for application on, for example, a patient's back or legs. However, the pad 12 need not be planar and square-shaped and may comprise any shape and be non-planar to lit around a joint, for example, a patient's knee. In this embodiment, the covering 24 comprises polymer sub-layer with a cloth outer layer which provides a flexible device which can conform to a part while the cloth cover provides insulation from the heating element to prevent burns. However, it should be understood that the pad may be constructed of any material known in the art such as, but not limited to, vinyl, PVC, rubber, felt, polymer and composite materials. Preferably, the cover is permanently attached to the heating pad 10.

Figure 2:
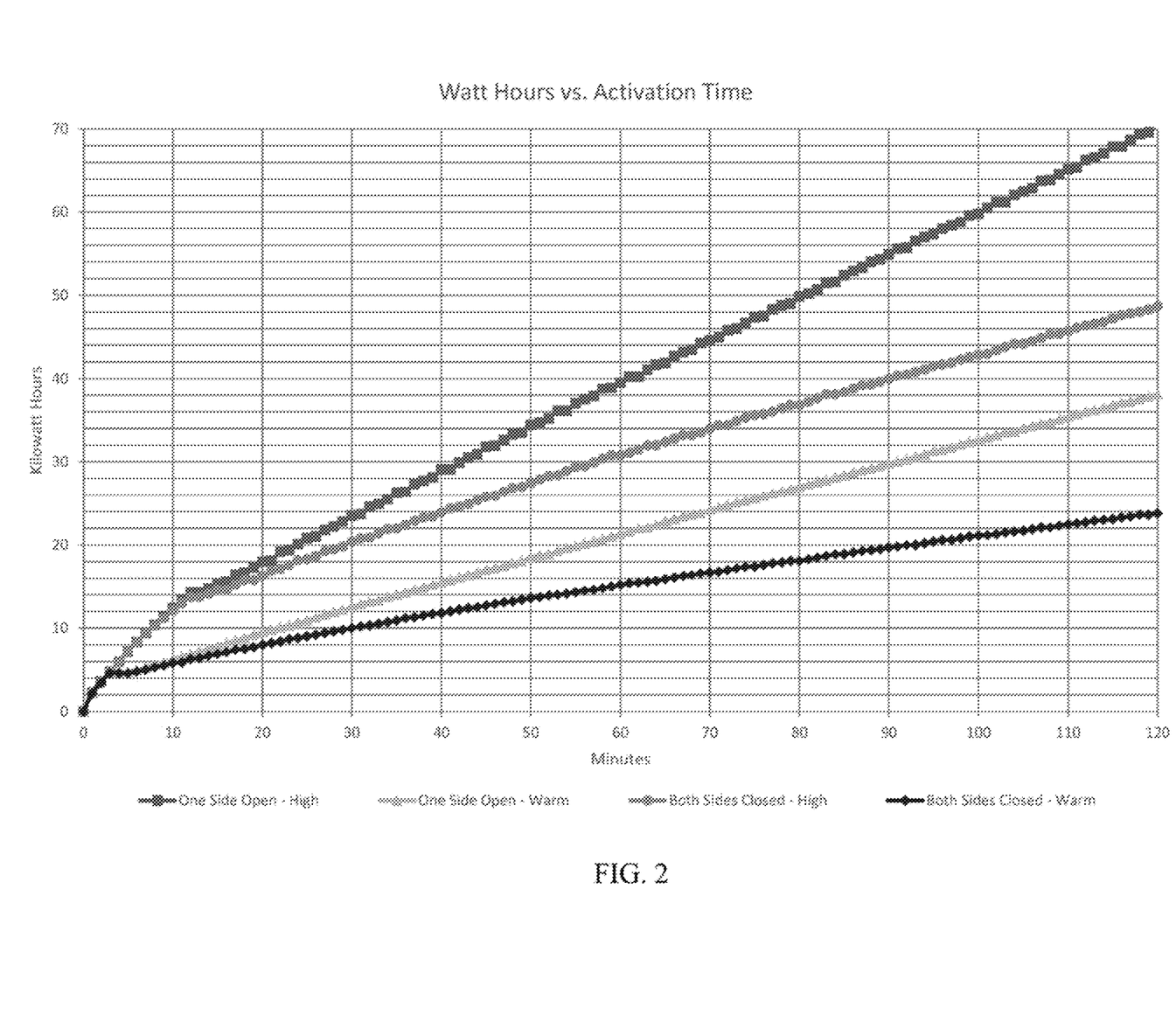
FIG. 2 is a plot of four curves each representing one of four conditions of a heating pad in an uncovered or covered state.

FIG. 2 is a plot of four curves of Watt Hour v. Application Time for the following four conditions of a tested heating pad:
1. High temperature setting, heating pad sandwiched between two 1" thick felt pads;
2. High temperature setting, heating pad in an open face sandwich with a single 1" felt pad;
3. Warm temperature (the lowest) setting, heating pad sandwiched between two 1" thick felt pads;
4. Warm temperature (the lowest) setting, heating pad in an open face sandwich with a single 1" felt pad.

The curves of FIG. 2 do not cross one another and they are distinct. At any time value each curve represents a unique total energy output which has been given in Watt-hours, although any metric, such as BTUs, calories, foot pounds, or kilowatt hours, can be used to represent the total energy. In embodiments of this invention, the total energy output is used as a statistical variant or diagnostic to indicate whether a heating pad is closed on both sides or open on one side. This diagnostic can be a robust indicator of the condition of the heating pad. When the heat output is the greatest for a given setting such as high, it indicates that the heating pad is being cooled on one side and not compressed by mechanical forces. These two notions result in a lower temperature at the interface between the heating pad and the patient's skin.

Embodiments of this invention include a method of monitoring the heating pad to prevent skin burns by monitoring an electric power usage of the heating pad and determining an improper covering of the heating pad from a predetermined variation in the electric power usage, such as the curve variation shown in FIG. 2. For a particular heating pad, the pad can be shut off or have power reduced if the power usage matches or otherwise correlates to a predetermined value of power usage. The predetermined values can be an established maximum or minimum, or a value or range of values for a predetermined time frame, such as represented by the curves in FIG. 2. The method can be implemented coded software instructions stored on a recordable medium in the control box 16 described for FIG. 1 above.

Figure 3:
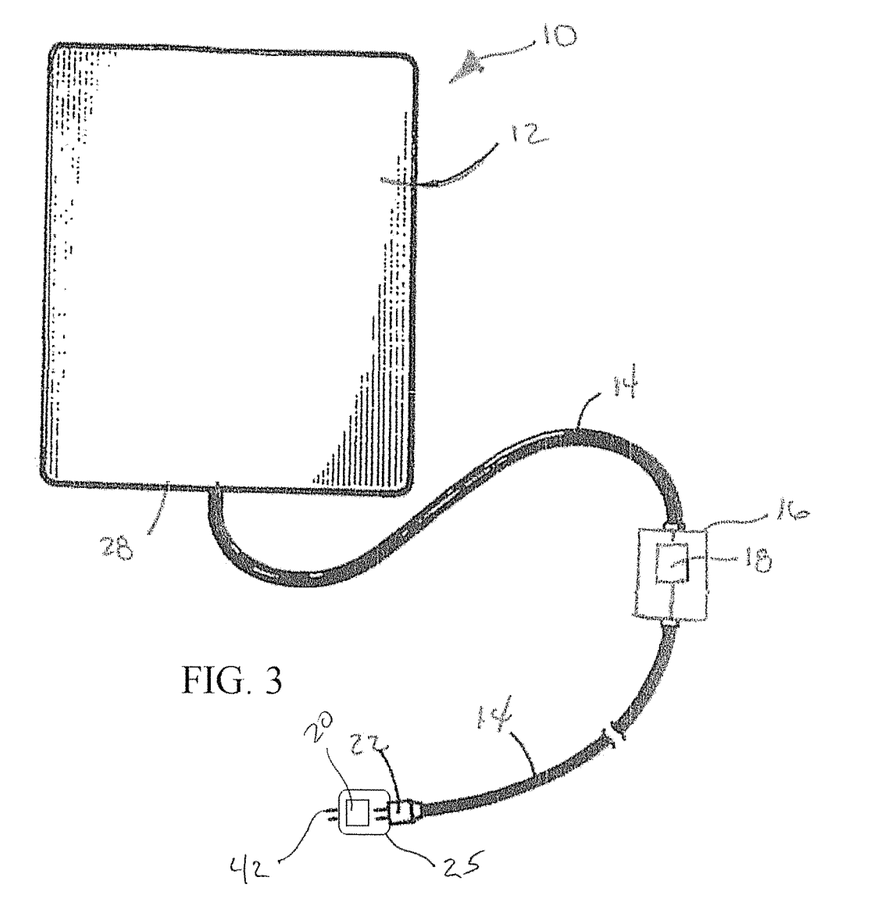
FIG. 3 is a top view of the electric heating pad according to an embodiment of this invention.

FIG. 3 shows an embodiment of a mechanism 25 for measuring and/or determining a power usage of electric heating pad 10, which can eliminate or reduce skins burns by detecting when both sides of the electric heating pad are covered and desirably lowering the output of or shutting off the pad. The electric heating pad 10 comprises a pad 12, a cord 14, a control box 16 including an on/off switch 18, and a plug 22.

In FIG. 3, the mechanism 25 is embodied in or as a separate attachment for the heating pad, requiring no change to the heating pad. The mechanism 25 receives the plug 22 of the heating pad 10, and includes its own plug 42 for insertion into a power source, such as a wall electrical outlet. The power for the heating pad 10 flows through the mechanism 25 and to the heating pad 10 for operation, and can be monitored as discussed herein.

The mechanism 25 includes or is embodied as a housing enclosing a processor and/or a programmed controller 20 having or in combination with any suitable components for measuring and/or determining a power usage of the pad 10. In embodiments of this invention, the mechanism is a programmable logic controller (PLC) or equivalent controller in combination with, for example, an ammeter, a voltmeter, or multimeter, along with a suitable calculation algorithm, all which can be embodied within the housing.

Figure 4:
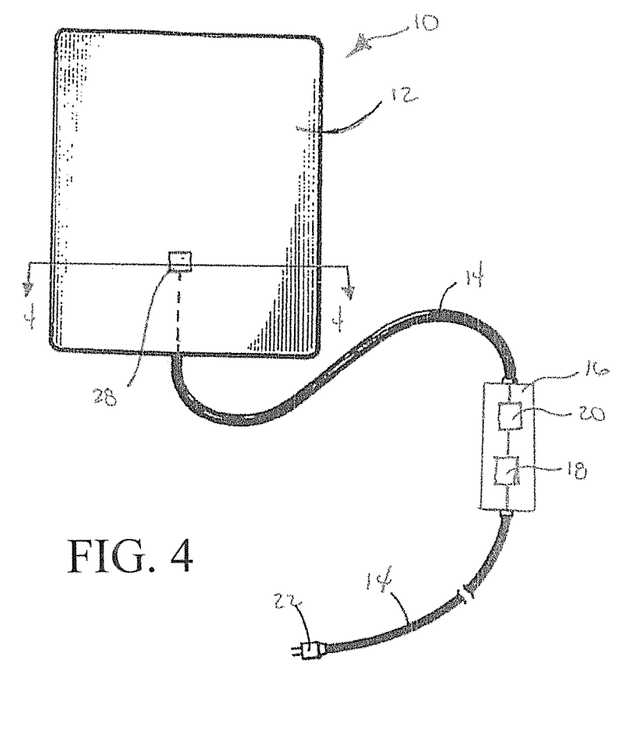
FIG. 4 is a top view of an electric heating pad according to an embodiment of this invention.
Figure 5:
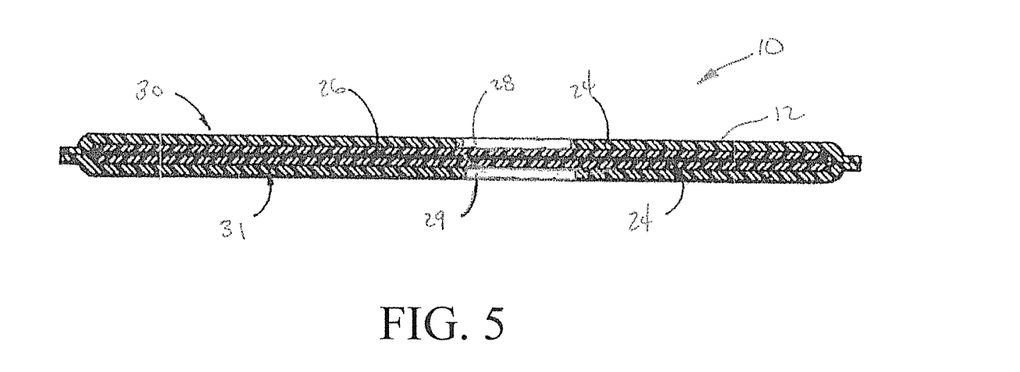
FIG. 5 is a cross-sectional view of the electric heating pad of FIG. 4.

FIGS. 4 and 5 show a further embodiment of an electric heating pad 10 of this invention which can eliminate or reduce skins burns by detecting when both sides of the electric heating pad are covered and shutting off the device.

The electric heating pad 10 of this invention seeks to prevent skin burns by: monitoring an absolute temperature of each surface of the heating pad 10; monitoring a temperature difference between each surface of the heating pad 10, where a small temperature difference indicates that both sides of the heating pad 10 are covered; and by monitoring a duty cycle of the heating pad 10, where a large off portion of the duty cycle indicates both sides of the heating pad 10 are covered.

As shown in FIGS. 4 and 5, the electric heating pad 10 according to an embodiment of this invention comprises a pad 12, a cord 14, a control box 16 including an on/off switch 18 and a processor 20, and a plug 22. The processor 20 preferably comprises a programmable logic controller. The pad 12 preferably includes a cover 24 surrounding a heating element 26. In this embodiment, the pad 12 is generally planar with a square-shape, usefully for application on, for example, a patient's back or legs. However, the pad 12 and covering 24 can be any suitable size, shape or material, as discussed above.

As best shown in FIG. 5, the pad 12 further comprises a pair of thermocouples 28, 29 adjacent to a first surface 30 of the pad 12 and a second surface 31 of the pad 12. The pair of thermocouples 28, 29 are electrically connected to the programmable logic controller to measure a temperature of the first surface 30 and the second surface 31. In an alternative embodiment, another device known to one of skill in the art may be used to measure the temperature of the surfaces 30, 31 of the pad 12. In the embodiment of FIG. 5, the thermocouples 28, 29 are integrated with the cover 24. Alternatively, the thermocouples may be integrated with the heating element 26 or mounted to a surface of the cover 24.

In operation according to one embodiment of this invention, the processor 20 receives the first surface temperature ($T_1$) from the first thermocouple 28 and the second surface temperature ($T_2$) from the second thermocouple 29. If either temperature exceeds a maximum temperature ($T_{max}$) the processor 20 shuts off the heating element 26. In a preferred embodiment, the maximum temperature ($T_{max}$) is specified. The maximum temperature can be set in the processor to act as a limiting operating temperature monitor and back up possible internal control thermostats malfunction.

The processor 20 also calculates a temperature difference ($T_{diff}=T_1-T_2$) between the first surface 30 temperature ($T_1$) and the second surface 31 temperature ($T_2$). If the processor detects a temperature difference ($T_{diff}=T_1-T_2$) that is less than a minimum temperature difference ($T_{diff,min}$) the programmable logic controller 20 shuts off the heating element 26. When the temperature difference ($T_{diff}=T_1-T_2$) is less than a minimum temperature difference ($T_{diff,min}$) it indicates that both surfaces 30, 31 of the heating pad 10 are covered. The minimum temperature difference ($T_{diff,min}$) can vary greatly depending on the design of the heating pad 10 and can, for example, be selected to vary from 1° F. to 30° F. or more. In an embodiment of this invention, the minimum temperature difference ($T_{diff,min}$) was selected to be 6° F. to initiate a shutdown of the heating element.

In a preferred embodiment, the processor 20 receives the heating duty cycle ($\tau$) of the heating element 26. The heating duty cycle ($\tau$) comprises a repeating period which includes an on portion where the heating element 26 receives current and heating the element up and an off portion where the heating element 26 does not receive current. The processor 20 monitors the duty cycle to calculate a ratio that the heating pad is off $$(R_{off}), R_{off} = \frac{t_{off}}{t_{on}+t_{off}} = \frac{t_{off}}{\tau},$$

where $t_{off}$ is the portion of the duty cycle the heating element 26 is off and $t_{on}$ is the portion of the duty cycle the heating element 26 is on. When the processor 20 calculates the $R_{off}$ as greater than a maximum allowable ratio ($R_{off, max}$), indicating that both surfaces 30, 31 of the heating pad 10 are covered, the processor 20 shuts off the heating element 26 to prevent burns. The maximum allowable ratio ($R_{off}$) can vary greatly depending on the design of the heating pad 10 and can, for example, be selected to vary from 0.30 to 0.90. In an embodiment of this invention, the maximum allowable ratio ($R_{off, max}$) was selected to be 0.70 to initiate a shutdown of the heating element. In a preferred embodiment, the $R_{off}$ is calculated as an average of a plurality of duty cycles to compensate for fluctuations in the duty cycle. In an alternative embodiment, the processor of this invention may monitor the ratio that the heating pad is off ($R_{off}$) to detect a change in the $R_{off}$ over a period of time ($\Delta R_{off}$). When the processor detects a change exceeding a set limit ($\Delta R_{off, max}$), the processor shuts off the heating element to prevent skin burns. The maximum allowable change in the $R_{off}$ over a period of time ($\Delta R_{off, max}$) can vary greatly depending on the design of the heating pad 10 and can, for example, be selected to range from 0.01 change to 0.20 change or more. In an embodiment of this invention, the maximum allowable change in the $R_{off}$ over a period of time ($\Delta R_{off}$) was selected to be 0.07, or approximately a 12% change in $R_{off}$, to initiate a shutdown of the heating element.

In a preferred embodiment, the heating pad 10 further includes either a dead-man switch or a timed switch to prevent burns due to users falling asleep during use.

Experiment—Surface Temperatures

Covering both sides of a pad during therapy causes the temperature and heat transfer at the interface between the heating pad and the body to increase to dangerous levels. In this experiment, a heating pad, a model HP-110 heating pad manufactured by KAZ, Inc., was tested for 120 minutes at the high control setting. A pair of K-type thermocouples were attached at the geometric center of vinyl faces of the heating pad. The experiment was conducted by placing the test pad on top of an application surface that roughly approximated the behavior of a human body. The temperature of application surface was measured to be 88° F., about 6° F. cooler than a human body surface temperature of 94° F.

The temperature measured by the thermocouple in contact with the application surface was designated $T_1$ and the other thermocouple temperature was designated $T_2$. With the test pad set on high and the top surface exposed to the environment, the temperatures $T_1$ and $T_2$ were monitored for 60 minutes; the values are tabulated in Table 2.

TABLE 2

| Time (min.) | Body Side $T_1$ (° F.) | Top Side $T_2$ (° F.) |
|---|---|---|
| 0 | 72.9 | 72.8 |
| 5 | 142.0 | 130.7 |
| 10 | 150.9 | 127.6 |
| 15 | 142.1 | 122.1 |
| 20 | 140.0 | 121.2 |
| 25 | 139.4 | 120.9 |
| 30 | 138.9 | 119.6 |
| 35 | 139.0 | 119.4 |
| 40 | 138.8 | 180.0 |
| 45 | 139.1 | 119.7 |
| 50 | 139.2 | 120.0 |
| 55 | 138.6 | 119.4 |

At the end of the first 60 minute interval, the top surface of the test pad was covered with a ½ inch thick felt pad and monitored for an additional 60 minutes until completion of a two hour test run. The temperatures $T_1$ and $T_2$ associated with this insulated phase of the testing program are displayed in Table 3.

TABLE 3

| Time (min.) | Body Side $T_1$ (° F.) | Top Side $T_2$ (° F.) |
|---|---|---|
| 60 | 139.4 | 121.2 |
| 65 | 140.0 | 126.5 |
| 70 | 141.3 | 132.4 |
| 75 | 142.4 | 132.6 |
| 80 | 141.6 | 136.4 |
| 85 | 141.9 | 137.6 |
| 90 | 141.8 | 138.3 |
| 95 | 141.6 | 138.2 |

TABLE 3-continued

| Time (min.) | Body Side $T_1$ (° F.) | Top Side $T_2$ (° F.) |
|---|---|---|
| 100 | 141.4 | 138.2 |
| 105 | 141.4 | 139.7 |
| 110 | 141.3 | 138.1 |
| 115 | 141.1 | 138.1 |
| 120 | 142.3 | 139.1 |

Figure 6:
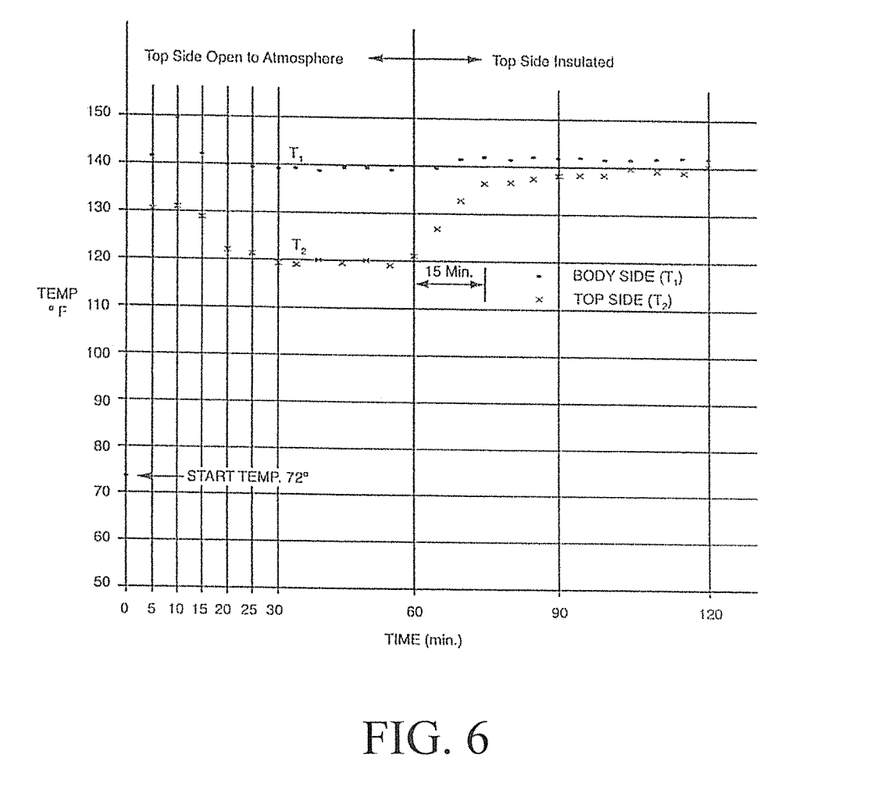
FIG. 6 is a graph showing experimental data of surface temperatures of a heating pad in an uncovered and covered state.

The results of the testing program are summarized in FIG. 6. The following observations are noteworthy:
a. Top side open to atmosphere
  i. The start-up temperature was 72° F.
  ii. In the first 10 minutes, $T_1$ overshoots to about 150° F. before returning to a steady state temperature of 138° F.
  iii. $T_1$ remained steady at 138° for about 50 minutes.
  iv. The temperature $T_2$ exhibits a similar response, overshoots to about 130° F. and returns to a steady state of about 118° F. for the next 40 minutes.
  v. The programmable logic controller (PLC) recorded a steady state temperature difference $(T_1-T_2)$ of 20° F. when the test pad had its top side open to the atmosphere.
b. Top side insulated
  i. After 60 minutes the top side of the test pad was insulated with a felt pad.
  ii. Over the next 15 minutes, $T_1$ rose from 138° F. to 142° F.
  iii. Within 15 minutes, $T_2$ rose from 118° F. to 136° F.
  iv. Over the next 40 minutes $T_1$ is stable and $T_2$ gradually increases to within 5° to 6° F. of $T_1$.

From this data, the PLC recorded that the initial steady state difference $(T_1-T_2)$ of 20° F. becomes a 6° F. difference in 15 minutes when the top side is covered. This change in $(T_1-T_2)$ reflects the physical application of an insulated cover of the top side. Using this data, a heating pad can be designed to shut off the heating element to prevent burns when the $(T_1-T_2)$ is less than 7° F. to protect the user from this "covering misuse."

Further, using this data, the heating pad can be designed to provide an additional layer of protection, the PLC can shut off the heating pad when the $T_1$ exceeds, for example, 140° F., as an emergency measure.

Experiment—Duty Cycle Control

A heating element will draw more energy to maintain a steady state heating pad temperature when one face of the pad is uncovered because some energy is expended to the environment. Consequently, the on/off electrical demand spends more time in the "on" state when a heating pad face is uncovered as opposed to covered. If the average heating times are stable and significantly different in the covered and uncovered states, a small difference in the average heating time provides a criterion for shutting off the heating pad before skin burns occur. No additional hardware, thermocouples, or wiring is required. Only control logic and monitoring activities are incorporated to provide a primary or secondary safety system.

In this experiment, the PLC was programmed to measure the period of an on/off duty cycle. The duty cycle period ($\tau$) of this type of control is the sum of time on ($t_{on}$) plus time off ($t_{off}$), $\tau = t_{on} + t_{off}$. The duty cycle is a stochastic variable so in this experiment an average of ten cycles was used to describe this period. Using this cycle period, a ratio $\overline{R}_{off}$ was then defined as $$\overline{R}_{off} = \frac{\overline{t}_{off}}{\overline{t}_{on} + \overline{t}_{off}} = \frac{\overline{t}_{off}}{\tau},$$

where the over bar symbol denotes an average.

Using the same set up described above in the previous experiment, a two hour test run was undertaken to study the duty cycles with the heating pad in the uncovered and covered states. The test protocol is characterized as follows:
  i. The test pad was set on high and placed onto the application surface.
  ii. For various 5 minute intervals, ten values of $t_{on}$ and $t_{off}$ were measured with the top surface of the heating pad open to the atmosphere.
  iii. Step (ii) was then repeated with the top surface covered with a felt pad.
  iv. The felt pad was then removed and, after a delay, step (ii) was repeated.

The observed duty cycle data is tabulated in Table 4.

TABLE 4

| Run Time (min.) | $i_{on}$ | $i_{off}$ | $\overline{R}_{off}$ | Cover |
|---|---|---|---|---|
| 5-10 | 6.9 | 13.8 | 0.666 | Off |
| 10-15 | 9.5 | 15.3 | 0.610 | Off |
| 15-20 | 10.6 | 16.9 | 0.614 | Off |
| 20-25 | 12.5 | 20.3 | 0.618 | Off |
| 25-30 | 16.1 | 23.4 | | Off |
| 60-65 | 16.5 | 24.9 | 0.600 | On |
| 65-70 | 15.7 | 31.0 | 0.664 | On |
| 70-75 | 17.0 | 40.2 | 0.702 | On |
| 75-80 | 14.7 | 39.9 | 0.730 | On |
| 85-90 | 16.6 | 40.0 | 0.709 | On |
| 90-95 | 17.0 | 47.9 | 0.738 | On |
| 95-100 | 15.1 | 52.8 | 0.777 | On |
| 110-115 | 18.6 | 33.7 | 0.644 | Off |
| 115-120 | 21.5 | 35.0 | 0.619 | Off |

From the data in Table 4, the mean value of the seven averages for $R_{off}$ associated with the uncovered test pad is 0.6230. The corresponding mean of seven averages $R_{off}$ for the covered test pad is 0.7029. Covered $R_{off}$–Uncovered $R_{off}$=0.0799. The inactive time $t_{off}$ increased 12.83% when the heating pad was covered. Using this data, a heating pad can be designed to shut off the heating element to prevent burns when the $R_{off}$ exceeds 0.700 or when the change in $R_{off}$ exceeds 12%.

Thus, the invention provides an improved heating pad which includes a pair of thermocouples and a processor to prevent skin burns due to covering both sides of a heating pad by: monitoring an absolute temperature of each surface of the heating pad; monitoring a temperature difference between each surface of the heating pad, where a small temperature difference indicates that both sides of the heating pad are covered; and by monitoring the duty cycle of the heating element, where a large off portion of the duty cycle indicates both sides of the heating pad are covered.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method of monitoring a heating pad to prevent skin burns comprising monitoring an electric power usage at a power cord of the heating pad with a power measurement mechanism in combination with the power cord of the heating pad, and determining an improper covering of the heating pad by the power measurement mechanism comparing the monitored electric power usage to a predetermined variation in the electric power usage, wherein the predetermined variation is stored in the power measurement mechanism.

2. The method of claim 1, further comprising automatically turning off the heating pad upon the determining the improper covering.

3. The method of claim 1, wherein the determining comprises meeting or exceeding a predetermined value stored in the power measurement mechanism.

4. The method of claim 3, wherein the predetermined value is a maximum value, a minimum value, or within a range of values for a predetermined time frame.

5. The method of claim 3, wherein the determining comprises: meeting or exceeding the predetermined value for a predetermined amount of time.

6. The method of claim 1, wherein the heating pad includes a controller performing the step of comparing the monitored electric power usage to a predetermined variation in the electric power usage, and the controller turning off a heating element upon the determining by the controller of meeting or exceeding the predetermined variation in the electric power usage.

7. The method of claim 1, wherein the heating pad includes a controller and sensor monitoring total energy output of the heating pad.

8. The method of claim 1, wherein a maximum heat output indicates a properly used heating pad.

9. The method of claim 1, further comprising reducing power as a function of the predetermined variation in the electric power usage.

10. The method of claim 1, wherein the power measurement mechanism is in a control box that receives an electric plug of the power cord.

11. The method of claim 10, wherein the measurement mechanism comprises an ammeter, a voltmeter, or a multimeter within the control box in combination with a programmable logic controller.

12. A method of monitoring a heating pad to prevent skin burns comprising:
automatically measuring at a power cord extending from the heating pad an electric power usage of the heating pad; and
determining an improper covering of the heating pad by comparing the measured electric power usage to an established metric of electric power usage and the measured electric power usage meeting or exceeding the established metric of electric power usage.

13. The method of claim 12, further comprising automatically reducing power of, or turning off, the heating pad upon the determining the improper covering.

14. The method of claim 12, wherein the metric is a maximum value, a minimum value, or within a range of values for a predetermined time frame.

15. The method of claim 12, wherein the heating pad includes a controller and sensor at a surface of the heating pad for monitoring a total energy output of the heating pad.

16. The method of claim 12, wherein a maximum heat output indicates a properly used heating pad.

17. The method of claim 12, determining an improper covering is obtained by the measuring at and through the power cord without additional wiring within the heating pad.

18. The method of claim 12, wherein a monitoring device is in measurement combination with the power cord.

19. The method of claim 18, wherein a monitoring device receives a plug of the heating pad, and is connected to a power supply.

20. The method of claim 19, wherein the monitoring device comprises an ammeter, a voltmeter, or a multimeter, a calculation algorithm, and a second plug.

* * * * *